United States Patent
Walte et al.

(10) Patent No.: US 7,227,136 B2
(45) Date of Patent: Jun. 5, 2007

(54) METHOD AND ARRANGEMENT FOR DETECTING HARMFUL SUBSTANCES

(75) Inventors: Andreas Walte, Schwerin (DE); Wolf Münchmeyer, Schwerin (DE)

(73) Assignee: Airsense Analytics GmbH, Schwerin (DE)

( * ) Notice: Subject to any disclaimer, the term of this patent is extended or adjusted under 35 U.S.C. 154(b) by 0 days.

(21) Appl. No.: 11/219,645

(22) Filed: Sep. 7, 2005

(65) Prior Publication Data

US 2006/0219892 A1    Oct. 5, 2006

Related U.S. Application Data

(63) Continuation of application No. PCT/DE04/00427, filed on Mar. 4, 2004.

(30) Foreign Application Priority Data

Mar. 7, 2003    (DE) .................................. 103 10 394

(51) Int. Cl.
*H01J 49/00*    (2006.01)
*B01D 59/44*    (2006.01)

(52) U.S. Cl. ..................... 250/288; 250/287; 250/286; 250/282; 250/281; 250/424; 250/435

(58) Field of Classification Search .................... None
See application file for complete search history.

(56) References Cited

U.S. PATENT DOCUMENTS

| | | | |
|---|---|---|---|
| 2,959,677 A | 11/1960 | Robinson et al. | |
| 3,621,240 A | 11/1971 | Cohen et al. | |
| 3,631,436 A | 12/1971 | Taguchi | |
| 3,925,183 A | 12/1975 | Oswin et al. | |
| 4,311,669 A | 1/1982 | Spangler | |
| 4,551,624 A | 11/1985 | Spangler et al. | |
| 4,987,767 A | 1/1991 | Corrigan et al. | |
| 6,636,811 B1 * | 10/2003 | Walte et al. | 702/24 |
| 6,946,671 B2 * | 9/2005 | Smith et al. | 250/559.4 |

\* cited by examiner

*Primary Examiner*—Nikita Wells
(74) *Attorney, Agent, or Firm*—Walter Ottesen

(57) ABSTRACT

A method and an arrangement detect harmful substances while eliminating or minimizing the drawbacks of an ion-mobility spectrometer (IMS). The sample gas flow is mixed with a reference gas utilizing a pump (7). A reaction gas is supplied via a metering unit (10) to the ion-mobility spectrometer (2) when complex ion-mobility spectrometer spectra are present. The measurement signals obtained as to the gas-quantity ratio between the sample gas and the reference gas are adapted to the original concentration and are then compared to previously defined and stored measured values via a signal height comparison or a pattern recognition. The measuring system is rinsed following the measurement phase by feeding the reference gas and is cleaned by metering an additional cleansing gas when harmful substances are detected which could not be rinsed away. Such methods and measuring systems are used for identifying harmful substances in ambient air.

22 Claims, 1 Drawing Sheet

METHOD AND ARRANGEMENT FOR DETECTING HARMFUL SUBSTANCES

CROSS REFERENCE TO RELATED APPLICATIONS

This is a continuation of international patent application PCT/DE04/00427, filed Mar. 4, 2004, and claiming priority from German patent application no. 103 10 394.5, filed Mar. 7, 2003, and the entire content of both applications is incorporated herein by reference.

FIELD OF THE INVENTION

The invention relates to a method for determining gaseous harmful substances utilizing a combination of an ion mobility spectrometer and additional detectors which detect harmful substances which cannot be detected by the ion mobility spectrometer. The invention is also directed to an arrangement for carrying out the method of the invention.

BACKGROUND OF THE INVENTION

Methods and measuring systems of the above kind are utilized for identifying harmful substances in ambient air. The detection of harmful substances after accidents or catastrophes is important, for example, for emergency personnel of fire and police departments. A list of thirty-three of the most frequently encountered harmful substances has been prepared for this reason in Germany for the protection of emergency personnel. This list includes also concentrations, the so-called emergency tolerance values (ETV list), at which one can assume that it is possible to safely work without breathing protection over a time period of four hours. At the present time, work is ongoing on an expansion of the list while considering the international acute exposure guide line levels (AEGL).

For military personnel and most recently also for civilian emergency personnel, especially the additional detection of chemical warfare substances or explosives is of interest.

These harmful substances can be detected partially with measuring systems which primarily comprise individual gas detectors or combinations of different gas detectors. The measurement signals of the individual gas detectors can then be compared to signals measured in advance or stored and the measured state can be described. As detectors, the following are, for example, appropriate: photo-ionization detectors (PID), electrochemical cells (EC) and metal-oxide sensors (MOS). Measuring apparatus, which supply two-dimensional data, that is, spectra, are also used. Examples of these are mass spectrometers (MS), Fourier transform infra-red spectrometers (FTIR) or ion mobility spectrometers (IMS).

Simple detectors such as a PID, MOS or EC are suitable for the detection of many harmful substances with their detecting limits in the upper ppb range or lower ppm range. However, these detectors are too insensitive for detecting warfare materials. Furthermore, their selectivity is often insufficient in order to detect harmful substances with the necessary reliability.

U.S. Pat. No. 2,959,677 discloses the essential functional features of a PID. With the aid of a UV lamp, the gas to be detected is ionized and thereafter is electrically detected. What is primarily significant is the ionization potential of the compound to be detected. In the event that the energy of the UV-radiation is greater than the ionization energy of the compound, then these energies can be detected. What is disadvantageous here is that many harmful substances cannot be detected. There is no spectral information supplied. Furthermore, it is disadvantageous that PID-lamps are rapidly contaminated which leads to poorer signal exploitation.

U.S. Pat. No. 3,631,436 discloses the essential functional features of the metal oxide sensors. These sensors react with reducing and oxidizing gases. These sensors have a relatively intense cross sensitivity and cannot be used for detecting individual substances or as warning devices because of the high rate of false alarms. MOS sensors are characterized by very rapid response times after an exposure to gas; however, the sensors have the disadvantage that the decay times are significantly longer.

Electrochemical cells are more selective than MOS sensors. A determination of individual substances is nonetheless not possible with the detectors because, here too, cross sensitivities occur, that is, there are no electrochemical cells available for all substances. The essential functional features of the electrochemical cells are disclosed in U.S. Pat. No. 3,925,183.

The ion mobility spectrometers (IMS) or the plasma chromatograph are known for some time. In contrast to other spectrometers, no moveable or complex individual parts are needed in the IMS so that these systems can be built small and cost effectively. For many compounds, very low detecting limits in the ppt-ppb range can be achieved. For this reason, these systems have been utilized for years by the military to detect warfare substances. A description of the individual components in an IMS can be found, for example, in U.S. Pat. No. 3,621,240. The different mobility of ions is utilized by the IMS. These apparatus comprise an inlet system, an ion source, an electrical drift tube and a measurement sensor for detecting low electrical currents which are generated by the impinging ions. For the ion sources, radioactive Ni63 foils are typically used and, in the electrical drift tube, the ions are separated in accordance with their mobility at ambient pressure after a defined start by means of an electrically switched grating or grid. Primarily, air molecules are ionized in the ion source at atmospheric pressure. These air molecules thereafter ionize water clusters which are also referred to as reactant ions. Thereafter, the harmful substances are ionized via proton transfer reactions, electron transfer reactions or proton abstraction reactions. By changing the polarity of the drift path, positive ions can be detected in the positive operating mode or negative ions in the negative operating mode.

In mobile systems, the inlet is, as a rule, a membrane. A membrane inlet system for an IMS is described in U.S. Pat. No. 4,311,669. It is advantageous that, because of the membrane, the influences on the measuring signal via disturbance quantities are reduced which include, for example, moisture, pressure and temperature and, for this reason, IMS systems can be manufactured to be small and portable. It is disadvantageous that the membrane causes the measuring system to react with more inertia with respect to its response time.

What is especially disadvantageous in the IMS, is the long time duration which must be allowed to elapse until the system is again operationally ready for measurement after switching on the apparatus. The IM detector requires this time because the IM detector must flush disturbing substances out of the system which have accumulated during the switched-off state. It is furthermore disadvantageous that, for short-term overdosing, the system is no longer measurement ready and must be flushed for several minutes up to hours. It is also disturbing that the spectra are dependent on concentration.

A further problem is the in part low selectivity of the IMS. One reason is that, often, the harmful substances of interest are not ionized because of competing reactions in the ionization chamber and therefore cannot be detected. These competing reactions can lead to the situation that many harmful substances having lower proton affinities, such as many solvents, do not even appear in the spectrum, for example, in the presence of gases such as ammonia. On the other hand, the detection of warfare substances can be made more difficult or even impossible by the presence of solvents in high concentrations (ppm). The false alarm rate is then increased by the superposed spectra in a mixture of gases. Furthermore, warfare substances having low proton affinity or electron affinity are not determined with the required detection limits.

A further disadvantage of the IMS is the limited measuring range which, for example, for a beta radiator as ionization source, amounts to typically maximally two orders of magnitude. A quantitative statement is therefore difficult.

It is furthermore problematic that many harmful substances exhibit a low vapor pressure so that the detection limits of the detectors are not adequate in order to register these limits.

A publication of L. V. Haley entitled "Development of an Explosives Detection System using fast GC-IMS Technology" (Proceedings 32 Annual 1998 International Canada Conference, Alexandria, Va. USA (1998), pages 59 to 64) describes the combination of a gas chromatographic device with an ion mobility spectrometer (IMS).

U.S. Pat. No. 4,987,767 discloses a detection system for explosive gases. A vapor and/or a particle emission is conducted in a test chamber wherein a separation of the vapor mixture and/or particle emission takes place which is then supplied to a gas chromatographic device and an ion mobility spectrometer (IMS) for detailed substance analysis.

In the last two mentioned publications, it is disadvantageous that the measuring method is very complex and expensive because of the use of a gas chromatographic device.

Furthermore, a method is known from a publication by O. D. Sparkman (The Twelfth Sanibel Conference on Mass Spectrometry: Field-Portable and Miniature Mass Spectrometry; J. Am. Soc. Mass Spectrom. 11 (2000), pages 468 to 471) wherein a combination of an IMS and additional detectors is used to determine gaseous harmful substances. Here, with the additional detectors, the harmful substances are detected which are not detectable with the IMS because of their low proton affinities or low electron activity. However, in this publication, there is no suggestion as to in what manner the IMS is coupled to the additional detectors. Furthermore, there are no measures described which prevent the measuring range of the IMS to be exceeded or that there be a drop therebelow during the measurement.

SUMMARY OF THE INVENTION

It is an object of the invention to provide a method and an arrangement for detecting the above-mentioned harmful substances. It is a further object of the invention to compensate for or minimize the disadvantages of the IMS.

The method of the invention is for detecting gaseous harmful substances in a sample gas flow utilizing a measuring system including a metering unit for metering a reaction gas and a combination of an ion-mobility spectrometer and a plurality of detectors which detect those of the harmful substances not detectable by the ion-mobility spectrometer. The method includes the steps of: drawing the sample gas flow into the measuring system; with a pump, admixing a reference gas to the sample gas flow before the sample gas flow reaches the detectors or, alternatively, only before the sample gas flow reaches the ion-mobility spectrometer so as to cause the sample gas flow to be mixed with the reference gas in order to always maintain the concentration of the harmful substances supplied to the detectors below a predefined concentration; during the measurement, supplying the reaction gas via the metering unit to the ion-mobility spectrometer when complex ion-mobility spectrometer spectra are present in order to thereby increase the selectivity of the ion-mobility spectrometer; obtaining measurement signals from the ion-mobility spectrometer and the detectors as to a gas-quantity ratio between the sample gas and the reference gas; adapting the measurement signals to the original concentration of the harmful substances in the sample gas; thereafter, comparing the measurement signals to previously defined and stored measured values via a simple comparison of the signal heights or a pattern recognition wherein all detector signals are compared to previously stored signals at the same time; based on this comparison, issuing an alarm; and, rinsing the measuring system by supplying the reference gas thereto after the measuring phase and supplying an additional cleaning gas to cleanse the measuring system when harmful substances are detected which can not be rinsed.

The disadvantages set forth initially herein and associated with the state of the art are eliminated by the invention.

Some of the disadvantages of the IMS can be eliminated via suitable combinations of the IMS and other detectors. The additional detectors are to detect the harmful substances which are not measured by the IMS. A PID can detect, for example, the aromatics such as benzene. Further compounds such as phosgenes can be detected with electrochemical cells having lower detection limits. The cross sensitivity of the MOS sensors can be utilized in order to detect other harmful substances such as carbon monoxide. A further aid for improving the selectivity of the IMS can be realized via additional metered reaction gases. According to U.S. Pat. No. 4,551,624, the selectivity of the system is improved in the positive operating mode with respect to phosphor organic compounds, such as warfare substances, by the additional metering of acetone. The selectivity of the system improves in the negative operating mode with respect to nitrogen organic compounds, such as explosives, when carbon tetrachloride is used.

As mentioned above, the added metering of these reaction gases, however, leads to the situation that many of the other harmful substances are no longer detected. For this reason, an operation without admixing reaction gas is suggested for the general detection of harmful substances. To ensure a result, a reaction gas is admixed in the second step. Thus, for example, in the positive operating mode, acetone or ammonia can be used in order to make possible an improved and reliable detection of the warfare substances. In the negative operating mode, dichloromethane or carbon tetrachloride can be used in order to detect explosive compounds.

A controlled additional metering of a reference gas (such as purified fresh air at the inlet) can prevent that an excessive exposure of the IMS takes place. As a control variable for the dilution, the IMS or preferably a more rapid detector (such as a MOS sensor) can be used. Additionally, the measuring range of the IMS can, in this way, be improved by an order of magnitude of one to two.

The system can also be continuously flushed or rinsed with fresh air in the switched-off state in order to improve the measuring operational readiness of the measuring system after switch-on. A cleansing gas such as ozone from an ozone source can be additionally utilized in order to degrade contamination in the measuring system so that the system is more rapidly operationally ready.

BRIEF DESCRIPTION OF THE DRAWING

The invention will now be described with reference to the single FIGURE of the drawing (FIG. 1) which shows an arrangement for carrying out the method for determining gaseous harmful substances.

DESCRIPTION OF THE PREFERRED EMBODIMENTS OF THE INVENTION

Figure 1:
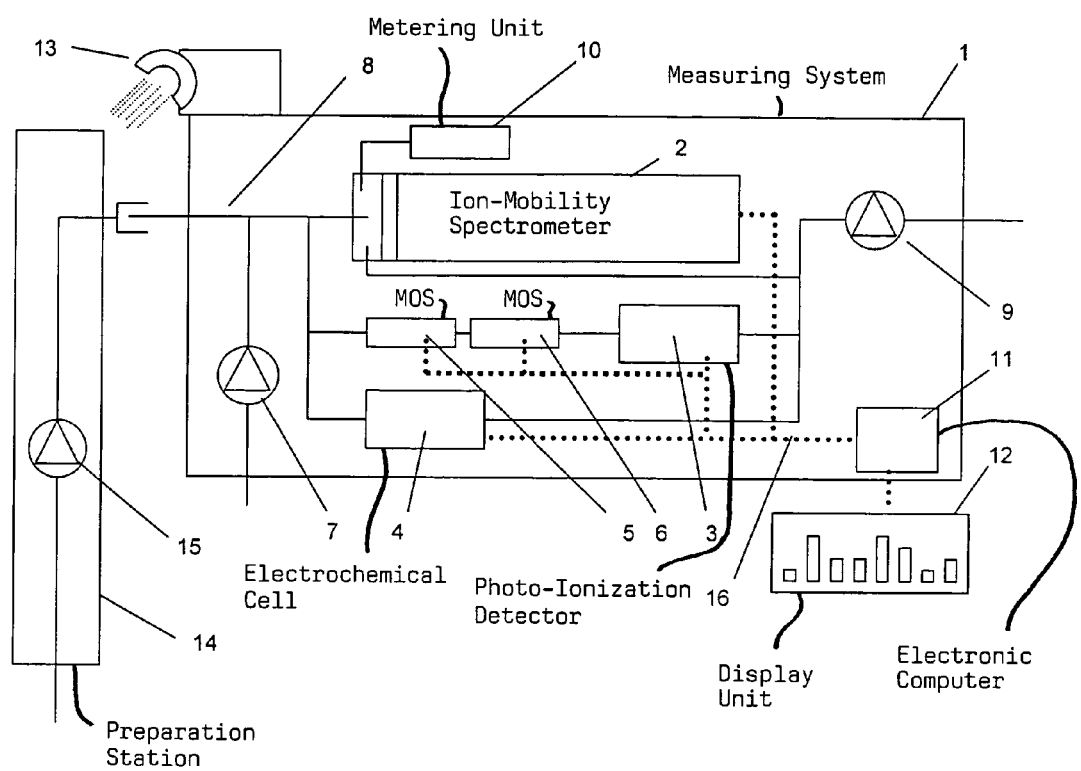

The arrangement of the invention primarily comprises a measuring system 1 which includes, for example, a combination of an IMS 2, a PID 3, an EC 4 and two MOS (5, 6). The gas to be measured is drawn by suction via a pump 9 and reaches the IMS and the other detectors via a split of the measurement gas path. The path to the other detectors is, in turn, subdivided into two paths. One path leads to the EC 4 and the other path leads via the MOS (5, 6) to the PID 3. The gas paths are thereafter brought together before they are connected to the pump 9.

The measuring system includes a further pump 7 for admixing a reference gas into the measurement gas path 8. The reference gas is drawn by suction by the above-mentioned pump 9. In order to go easy on the detectors, the measuring system is so operated that primarily the reference gas is measured. For low measuring signals, the flow rate of the pump 7 is reduced so that the portion of the ambient air to be measured increases. The admixing of the reference gas can take place via defined stages or even be controlled by the measuring signal of a detector.

When complex high IMS spectra are present or especially for justified reasons for suspicion, the selectivity of the IMS can be increased in that reaction gases are introduced into the IMS via a metering unit 10. In an evaluation of the measuring signals, the selectivity of the system can be improved by combinations of the spectra with and without reaction gases.

Electronic computers 11 prepare the data of the individual detectors and show the same acoustically or graphically via a display unit 12. By way of example, in the IMS, only the integrated measurement signals before and after the reactant ion peak can be used. Since the system can operate in the negative as well as in the positive operating mode, four measurement channels thereby result. In the above-described configuration, eight measurement channels are available together with the signals of the other detectors. It is understood that the spectra of the IMS can be also further subdivided so that significantly more than four channels can be applied for evaluation.

The channels can be used as input signals for a follow-on pattern detection. Simple distance classifiers (such as the distance classifier of Euclid) up to and including discrimination classifiers or even neuronal networks can be used here.

An illustration of the IMS spectra (with which the measuring signal of the IMS detector is shown as a function of time) is also possible and is necessary for identifying individual compounds such as warfare substances.

To investigate contaminated surfaces, an optional heat source 13 is used (which can, for example, warm the surfaces via infrared radiation) so that the compounds can be made volatile. Additionally, it is possible to provide the measuring system with a positioning method (for example, GPS) and with a memory. In this way, the measuring signals of the detectors can be assigned spatially and with respect to time.

In the event that the measuring system is not used, it is stored in a special preparation station 14 which includes a pump 15. The pump ensures that the system is continuously flushed with the reference gas. In this way, it is prevented that disturbing components can deposit in the measuring system. The measuring system is then operationally ready in a few minutes. The preparation station functions at the same time for charging the batteries and reading out the data stored in the system and can conduct the data to another location as required.

It is understood that the foregoing description is that of the preferred embodiments of the invention and that various changes and modifications may be made thereto without departing from the spirit and scope of the invention as defined in the appended claims.

What is claimed is:

1. A method for detecting gaseous harmful substances in a sample gas flow utilizing a measuring system including a metering unit for metering a reaction gas and a combination of an ion-mobility spectrometer and a plurality of detectors which detect those of said harmful substances not detectable by said ion-mobility spectrometer, the method comprising the steps of:

drawing said sample gas flow into said measuring system;

with a pump, admixing a reference gas to said sample gas flow before said sample gas flow reaches said detectors or, alternatively, only before said sample gas flow reaches said ion-mobility spectrometer so as to cause said sample gas flow to be mixed with said reference gas in order to always maintain the concentration of said harmful substances supplied to said detectors below a predefined concentration;

during the measurement, supplying said reaction gas via said metering unit to said ion-mobility spectrometer when complex ion-mobility spectrometer spectra are present in order to thereby increase the selectivity of said ion-mobility spectrometer;

obtaining measurement signals from said ion-mobility spectrometer and said detectors as to a gas-quantity ratio between said sample gas and said reference gas;

adapting said measurement signals to the original concentration of said harmful substances in said sample gas;

thereafter, comparing said measurement signals to previously defined and stored measured values via a simple comparison of the signal heights or a pattern recognition wherein all detector signals are compared to previously stored signals at the same time;

based on this comparison, issuing an alarm; and, rinsing said measuring system by supplying said reference gas thereto after the measuring phase and supplying an additional cleaning gas to cleanse said measuring system when harmful substances are detected which can not be rinsed.

2. The method of claim 1, wherein the mixing of the gaseous harmful substances with the reference gas (before reaching said detectors, alternatively also only before reaching said ion-mobility spectrometer) takes place in that said reference gas is admixed in defined quantities starting with the highest possible flow quantity which is later reduced, said gas flow is then supplied to said ion-mobility spectrometer or is split up and is conducted to said ion-mobility spectrometer and in parallel to said detectors.

3. The method of claim 1, wherein the measurement signal of one or several of said detectors is used to control the metering of said reference gas.

4. The method of claim 3, wherein one of said detectors is a rapid sensor and the relative signal height of said rapid sensor is used directly to provide a short-term increase of the gas flow of said pump in the event that the measurement signal of said rapid sensor increases or to reduce the gas flow of said pump in the event that said measurement signal of said sensor decreases.

5. The method of claim 4, wherein said rapid sensor is a metal-oxide sensor.

6. The method of claim 4, wherein the measurement signal of said ion-mobility spectrometer can be used to adjust the absolute ranges of the gas flow quantity of said reference gas in that the absolute signal heights can be used during a longer time frame in order to make possible the coarse adjustment of the pumped quantity of said reference gas of the gas flow, that is, the adjustment of the maximum and minimum ranges of the pumped quantity of said reference gas.

7. The method of claim 1, wherein one of said detectors is a photo-ionization detector and said gaseous harmful substances are conducted via a combination of said ion-mobility spectrometer and said photo-ionization detector for detecting aromatics and said sample gas flow is split and conducted directly to said ion-mobility spectrometer and in parallel to said detectors.

8. The method of claim 7, wherein another one of said detectors is an electrochemical cell for detecting individual substances including phosgene and still other ones of said detectors are metal-oxide sensors for detecting hydrocarbons and carbon monoxide when substances are present which can not be measured with said ion-mobility spectrometer and/or said photo-ionization detector.

9. The method of claim 1, wherein, directly after the detection of gaseous harmful substances of industrial sources, the method comprises the further step of starting a measuring operation for selectively detecting harmful substances having high proton or electron affinity in that, before or after normal measuring operation, one or different reaction gases are admix metered to said ion-mobility spectrometer via said metering unit for metering reaction gases; said reaction gases being characterized by slightly lower proton or electron affinities than said harmful substances to be detected and thereby making possible the detection at higher specificity because many disturbing compounds are not ionized and, thereafter, the measurement signals of the ion-mobility spectrometer are applied for evaluation or, when a reaction gas was used, the measurement signals of the ion-mobility spectrometer are applied with and without the reaction gas for evaluation.

10. The method of claim 9, wherein said harmful substances having high proton or electron affinity include chemical warfare substances and explosives.

11. The method of claim 1, wherein said measuring system is part of an arrangement which also includes a preparation station having a pump and wherein the method comprises cleaning or rinsing said detectors of said measuring system with a reference gas before and after a measuring phase to clear said detectors of measured gases or reaction gases; and, if harmful substances are detected which cannot be rinsed away, causing said pump of said preparation station to interrupt the flow of said reference gas for a short time; and, generating or pumping a cleaning gas through said measuring system in order to degrade contamination so that said measuring system is again immediately operationally ready.

12. An arrangement for determining gaseous harmful substances in a sample gas flow, the arrangement comprising:
a mobile measuring system including:
an ion-mobility spectrometer;
a plurality of detectors;
a pump for moving said gas flow;
gas lines for connecting said ion-mobility spectrometer and said plurality of detectors to said pump;
a metering assembly for controllably metering a reference gas ahead of said plurality of detectors;
a metering unit for metering a reaction gas ahead of said ion-mobility spectrometer;
an electronic computer connected to said detectors and to said spectrometer for receiving and evaluating measurement signals therefrom; and,
said arrangement further including a preparation station having a pump for rinsing and cleansing said measuring system.

13. The arrangement of claim 12, further comprising a display unit connected to said electronic computer.

14. The arrangement of claim 13, further comprising at least one of an optical warning signal transducer and an acoustic warning signal transducer.

15. The arrangement of claim 12, wherein a first one of said detectors is an electrochemical cell and a second one of said detectors is an arrangement of two metal-oxide sensors and a photo-ionization detector connected downstream of said two metal-oxide sensors; and, said gas lines are configured to define three gas paths; a first one of said gas paths leads to said ion-mobility spectrometer, a second one of said gas paths leads to said electrochemical cell and a third one of said gas paths leads to said arrangement of two metal-oxide detectors and a photo-ionization detector.

16. The arrangement of claim 15, said metering unit being positioned at said ion-mobility spectrometer; and, said metering unit being configured to include valve means for metering one or several reaction gases to said ion-mobility spectrometer.

17. The arrangement of claim 16, wherein said reaction gases are stored in any one of gas bottles, diffusion tubes and permeation vessels.

18. The arrangement of claim 12, further comprising a preparation station including: a pump for flushing and cleansing said measuring system; a source for a cleansing gas; and, a charging unit for batteries.

19. The arrangement of claim 18, wherein said source for a cleansing gas is a UV-lamp, such as the lamp used in the photo-ionization detector.

20. The arrangement of claim 12, further comprising a heat source for investigating a surface and with which harmful substances on said surface can be made volatile; and, said heat source being positioned on said measuring system.

21. The arrangement of claim 20, wherein said heat source is an infrared lamp.

22. The arrangement of claim 12, said measuring system further comprising a positioning system and a memory from which data can be read out and transmitted to a central computer for processing.

* * * * *